(12) United States Patent
Galasso (10) Patent No.: US 10,031,124 B2
(45) Date of Patent: *Jul. 24, 2018

(54) ANALYTE SENSOR PORTS

(71) Applicant: Abbott Diabetes Care Inc., Alameda, CA (US)

(72) Inventor: John R. Galasso, St. Helena, CA (US)

(73) Assignee: Abbott Diabetes Care Inc., Alameda, CA (US)

( * ) Notice: Subject to any disclaimer, the term of this patent is extended or adjusted under 35 U.S.C. 154(b) by 344 days.

This patent is subject to a terminal disclaimer.

(21) Appl. No.: 14/823,777

(22) Filed: Aug. 11, 2015

(65) Prior Publication Data

US 2015/0346184 A1   Dec. 3, 2015

Related U.S. Application Data

(63) Continuation of application No. 12/859,055, filed on Aug. 18, 2010, now Pat. No. 9,101,303, which is a continuation of application No. 12/539,217, filed on Aug. 11, 2009, now Pat. No. 9,125,603.

(51) Int. Cl.
    *G01N 33/487*    (2006.01)
    *G01N 27/26*     (2006.01)
    *G01N 21/17*     (2006.01)
    *A61B 5/145*     (2006.01)
    *A61B 5/1455*    (2006.01)
    *A61B 5/1468*    (2006.01)
    *H01R 13/52*     (2006.01)

(52) U.S. Cl.
    CPC ........ *G01N 33/487* (2013.01); *A61B 5/14532* (2013.01); *A61B 5/14546* (2013.01); *G01N 21/17* (2013.01); *G01N 27/26* (2013.01); *A61B 5/1455* (2013.01); *A61B 5/1468* (2013.01); *A61B 2562/0295* (2013.01); *A61B 2562/18* (2013.01); *A61B 2562/225* (2013.01); *G01N 2201/02* (2013.01); *H01R 13/5224* (2013.01)

(58) Field of Classification Search
    CPC ...... G01N 33/487; G01N 21/17; G01N 27/26; G01N 2201/02; A61B 5/14532; A61B 5/14546; A61B 5/1455; A61B 5/1468; A61B 2562/0295; A61B 2562/18; A61B 2562/225; H01R 13/5224
    See application file for complete search history.

(56) References Cited

U.S. PATENT DOCUMENTS

| | | |
|---|---|---|
| 4,545,382 A | 10/1985 | Higgins et al. |
| 4,613,325 A | 9/1986 | Abrams |
| 4,711,245 A | 12/1987 | Higgins et al. |
| 5,096,669 A | 3/1992 | Lauks et al. |
| 5,108,889 A | 4/1992 | Smith et al. |
| 5,262,035 A | 11/1993 | Gregg et al. |
| 5,262,305 A | 11/1993 | Heller et al. |
| 5,264,104 A | 11/1993 | Gregg et al. |
| 5,320,725 A | 6/1994 | Gregg et al. |
| 5,356,786 A | 10/1994 | Heller et al. |

(Continued)

*Primary Examiner* — Maris R Kessel
(74) *Attorney, Agent, or Firm* — Vorys, Sater, Seymour and Pease LLP (57) ABSTRACT

The present disclosure provides a contamination resistant sensor port which includes one or more sealing members positioned so as to limit and/or prevent internal contamination of the sensor port with fluids and/or particles present in the environment outside the sensor port.

19 Claims, 8 Drawing Sheets

(56) References Cited

U.S. PATENT DOCUMENTS

| | | |
|---|---|---|
| 5,509,410 A | 4/1996 | Hill et al. |
| 5,536,249 A | 7/1996 | Castellano et al. |
| 5,593,852 A | 1/1997 | Heller et al. |
| 5,601,435 A | 2/1997 | Quy et al. |
| 5,628,890 A | 5/1997 | Carter et al. |
| 5,772,688 A | 6/1998 | Muroki |
| 5,820,551 A | 10/1998 | Hill et al. |
| 5,822,715 A | 10/1998 | Worthington et al. |
| 5,899,855 A | 5/1999 | Brown et al. |
| 5,918,603 A | 7/1999 | Brown et al. |
| 5,925,021 A | 7/1999 | Castellano et al. |
| 6,071,391 A | 7/2000 | Gotoh et al. |
| 6,120,676 A | 9/2000 | Heller et al. |
| 6,121,009 A | 9/2000 | Heller et al. |
| 6,143,164 A | 11/2000 | Heller et al. |
| 6,144,837 A | 11/2000 | Quy et al. |
| 6,161,095 A | 12/2000 | Brown et al. |
| 6,175,752 B1 | 1/2001 | Say et al. |
| 6,270,455 B1 | 8/2001 | Brown et al. |
| 6,284,478 B1 | 9/2001 | Heller et al. |
| 6,299,757 B1 | 10/2001 | Feldman et al. |
| 6,338,790 B1 | 1/2002 | Feldman et al. |
| 6,377,894 B1 | 4/2002 | Deweese et al. |
| 6,461,496 B1 | 10/2002 | Feldman et al. |
| 6,503,381 B1 | 1/2003 | Gotoh et al. |
| 6,514,460 B1 | 2/2003 | Fendrock et al. |
| 6,514,718 B2 | 2/2003 | Heller et al. |
| 6,540,891 B1 | 4/2003 | Stewart et al. |
| 6,560,471 B1 | 5/2003 | Heller et al. |
| 6,591,125 B1 | 7/2003 | Buse et al. |
| 6,592,745 B1 | 7/2003 | Feldman et al. |
| 6,600,997 B2 | 7/2003 | Deweese et al. |
| 6,616,819 B1 | 9/2003 | Liamos et al. |
| 6,618,934 B1 | 9/2003 | Feldman et al. |
| 6,676,816 B2 | 1/2004 | Mao et al. |
| 6,730,200 B1 | 5/2004 | Stewart et al. |
| 6,736,957 B1 | 5/2004 | Forrow et al. |
| 6,746,582 B2 | 6/2004 | Heller et al. |
| 6,749,740 B2 | 6/2004 | Liamos et al. |
| 6,764,581 B1 | 7/2004 | Forrow et al. |
| 6,773,671 B1 | 8/2004 | Lewis et al. |
| 6,881,551 B2 | 4/2005 | Heller et al. |
| 6,893,545 B2 | 5/2005 | Catch et al. |
| 6,942,518 B2 | 9/2005 | Liamos et al. |
| 7,041,468 B2 | 5/2006 | Drucker et al. |
| 7,167,818 B2 | 1/2007 | Brown et al. |
| 7,179,421 B1 | 2/2007 | Ho |
| 7,299,082 B2 | 11/2007 | Feldman et al. |
| 2001/0000396 A1 | 4/2001 | Dordi et al. |
| 2002/0119711 A1 | 8/2002 | Van Antwerp et al. |
| 2003/0069331 A1 | 4/2003 | Teiichi et al. |
| 2003/0144608 A1 | 7/2003 | Kojima et al. |
| 2004/0186365 A1 | 9/2004 | Jin et al. |
| 2004/0254434 A1 | 12/2004 | Goodnow et al. |
| 2005/0177398 A1 | 8/2005 | Watanabe et al. |
| 2006/0025662 A1 | 2/2006 | Buse et al. |
| 2006/0091006 A1 | 5/2006 | Wang et al. |
| 2006/0189858 A1 | 8/2006 | Sterling et al. |
| 2006/0189895 A1 | 8/2006 | Neel et al. |
| 2006/0189926 A1 | 8/2006 | Hall et al. |
| 2006/0224141 A1 | 10/2006 | Rush et al. |
| 2007/0068807 A1 | 3/2007 | Feldman et al. |
| 2007/0095661 A1 | 5/2007 | Wang et al. |
| 2007/0108048 A1 | 5/2007 | Wang et al. |
| 2007/0199818 A1 | 8/2007 | Petyt et al. |
| 2007/0233395 A1 | 10/2007 | Neel et al. |
| 2007/0249921 A1 | 10/2007 | Groll et al. |
| 2008/0060196 A1 | 3/2008 | Wang et al. |
| 2008/0066305 A1 | 3/2008 | Wang et al. |
| 2008/0102441 A1 | 5/2008 | Chen et al. |
| 2008/0119709 A1 | 5/2008 | Wang et al. |
| 2008/0148873 A1 | 7/2008 | Wang et al. |
| 2008/0234559 A1 | 9/2008 | Arbogast et al. |
| 2008/0267823 A1 | 10/2008 | Wang et al. |
| 2009/0011449 A1 | 1/2009 | Karinka et al. |
| 2010/0064800 A1* | 3/2010 | Stafford ............ H01R 13/5224 73/431 |
| 2010/0065426 A1* | 3/2010 | Stafford ............ H01R 13/5224 204/403.02 |

* cited by examiner

Top View

FIG. 6B

Side View

FIG. 6C

Top View

FIG. 6D

Side View

ANALYTE SENSOR PORTS

BACKGROUND OF THE INVENTION

Analyte sensors are commonly used to monitor the level of an analyte in a body fluid. For example, diabetics use analyte sensors, e.g., in the form of analytical test strips, to monitor body glucose levels. Commonly, an analyte sensor is contacted with a bodily fluid and inserted into an analyte meter or other device capable of determining one or more analyte levels based on signals provided by the analyte sensor. The analyte sensor can be received by the analyte meter or other device either before or after a sample of body fluid is applied to the analyte sensor. The sensor receiving area of the device, commonly referred to as a "sensor port," provides an opening in the device for insertion of the analyte sensor. Consequently, the sensor port also provides an opening from the outside environment to the interior of the device. This exposure to the outside environment via the sensor port creates the potential for contaminating materials to enter the device's interior. As such contamination may affect internal components and/or interfere with the analysis results, there is interest in developing sensor ports which limit the potential for contamination.

SUMMARY OF THE INVENTION

The present disclosure provides a contamination resistant sensor port which includes one or more sealing members positioned so as to limit and/or prevent internal contamination of the sensor port with fluids and/or particles present in the environment outside the sensor port.

In a first aspect, the present disclosure provides a sensor port, which includes a housing, wherein the housing includes a body and a protruding member. The protruding member defines an entry slot configured to receive an analyte sensor. The sensor port according to the first aspect also includes a first sealing member positioned on the protruding member and circumscribing the protruding member, wherein the first sealing member is configured to form a seal between the sensor port and an electrical device.

In one embodiment of the sensor port according to the first aspect, the body defines a first opening and a second opening. The sensor port includes a second sealing member positioned on the body of the housing such that a seal is formed over the first opening. The sensor port also includes a third sealing member positioned on the body of the housing such that a seal is formed over the second opening. In one such embodiment, the second and third sealing members each include an adhesive backing which provides for attachment to the body of the housing. In one embodiment, where the second and third sealing members each include an adhesive backing which provides for attachment to the body of the housing, the second and third sealing members each include polyimide film tape.

In one embodiment of the sensor port according to the first aspect, the protruding member includes a channel which circumscribes the protruding member, wherein the first sealing member is positioned in the channel. In one such embodiment, the channel defines an oval.

In one embodiment of the sensor port according to the first aspect, the electrical device is an analyte meter. In one such embodiment, the analyte meter is a glucose meter. In one embodiment, where the analyte meter is a glucose meter, the analyte sensor is a glucose test strip.

In one embodiment of the sensor port according to the first aspect, the first sealing member is a compliant gasket material. In one such embodiment, the compliant gasket material includes an elastomeric material. In one embodiment, where the first sealing member is a compliant gasket material, the compliant gasket material is an o-ring.

In one embodiment of the sensor port according to the first aspect, the entry slot includes an internal beveled face.

In one embodiment of the sensor port according to the first aspect, the housing includes an injection molded plastic.

In one embodiment of the sensor port according to the first aspect, the housing includes a top portion and a bottom portion which are joined to form the sensor port.

In one embodiment of the sensor port according to the first aspect, the sensor port is integrated in and operably connected to an electrical device. In one such embodiment, the electrical device is an analyte meter. In one embodiment, the analyte meter is a glucose meter.

In another embodiment of the sensor port according to the first aspect, where the sensor port is integrated in and operably connected to an electrical device, the electrical device is an integrated continuous glucose monitor receiver.

In another embodiment of the sensor port according to the first aspect, where the sensor port is integrated in and operably connected to an electrical device, the electrical device is a medication delivery device. In one such embodiment, the medication delivery device is a pump. In one embodiment, the medication delivered by the medication delivery device is insulin.

In one embodiment of the sensor port according to the first aspect, the first sealing member provides a substantially fluid-tight seal between the sensor port and the electrical device.

In a second aspect, the present disclosure provides a medication delivery device, wherein the medication delivery device includes a sensor port. The sensor port includes a housing and a first sealing member. The housing includes a body and a protruding member, the protruding member defining an entry slot configured to receive an analyte sensor. The first sealing member is positioned on the protruding member and circumscribes the protruding member. The first sealing member forms a seal between the sensor port and the medication delivery device.

In one embodiment of the medication delivery device according to the second aspect, the body defines a first opening and a second opening. The sensor port includes a second sealing member positioned on the body of the housing such that a seal is formed over the first opening. The sensor port also includes a third sealing member positioned on the body of the housing such that a seal is formed over the second opening. In one such embodiment, the second and third sealing members each include an adhesive backing which provides for attachment to the body of the housing. In one embodiment, where the second and third sealing members each include an adhesive backing which provides for attachment to the body of the housing, the second and third sealing members each include polyimide film tape.

In one embodiment of the medication delivery device according to the second aspect, the protruding member includes a channel which circumscribes the protruding member, wherein the first sealing member is positioned in the channel. In one such embodiment, the channel defines an oval.

In one embodiment of the medication delivery device according to the second aspect, the analyte sensor is a glucose test strip.

In one embodiment of the medication delivery device according to the second aspect, the first sealing member is a compliant gasket material. In one such embodiment, the compliant gasket material comprises an elastomeric material. In one embodiment, where the first sealing member is a compliant gasket material, the compliant gasket material is an o-ring.

In one embodiment of the medication delivery device according to the second aspect, the entry slot includes an internal beveled face.

In one embodiment of the medication delivery device according to the second aspect, the housing includes an injection molded plastic.

In one embodiment of the medication delivery device according to the second aspect, the housing includes a top portion and a bottom portion which are joined to form the sensor port.

In one embodiment of the medication delivery device according to the second aspect, the medication delivery device is a pump. In one embodiment, the medication delivered by the medication delivery device is insulin.

In one embodiment of the medication delivery device according to the second aspect, the first sealing member provides a substantially fluid-tight seal between the sensor port and the medication delivery device.

These and other objects, features and advantages of the present disclosure will become more fully apparent from the following detailed description of the embodiments, the appended claims and the accompanying drawings.

BRIEF DESCRIPTION OF THE DRAWINGS

The invention is best understood from the following detailed description when read in conjunction with the accompanying drawings. It is emphasized that, according to common practice, the various features of the drawings are not necessarily to-scale. The dimensions of the various features are arbitrarily expanded or reduced for clarity. Included in the drawings are the following figures.

Before the present invention is further described, it is to be understood that this invention is not limited to particular embodiments described, as such may vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges, and are also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, the preferred methods and materials are now described. All publications mentioned herein are incorporated herein by reference to disclose and describe the methods and/or materials in connection with which the publications are cited.

As used herein and in the appended claims, the singular forms "a," "and," and "the" include plural referents unless the context clearly dictates otherwise. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

DETAILED DESCRIPTION OF THE INVENTION

As summarized above, the present disclosure is directed to a splash-proof sensor port which includes one or more sealing members positioned so as to prevent internal contamination of the sensor port with fluids and/or particles present in the environment outside the sensor port. In some embodiments, the sensor port may be included in, e.g., integrated with, an analyte meter or monitoring system, e.g., an in vitro analyte meter or an in vivo analyte monitoring system. Analyte meters and analyte monitoring systems suitable for use with the disclosed sensor ports include, for example, those available from Abbott Diabetes Care Inc. (Alameda, Calif.). Analyte meters may be electrochemical or optical meters, and may be configured to determine the level of one or more analytes, where analytes of interest include, but are not limited to, glucose, blood β-ketone, ketone bodies, lactate, acetyl choline, amylase, bilirubin, cholesterol, chorionic gonadotropin, creatine kinase (e.g., CK-MB), creatine, DNA, fructosamine, glucose, glutamine, growth hormones, hormones, ketones, lactate, peroxide, prostate-specific antigen, prothrombin, RNA, thyroid stimulating hormone, and troponin, in sample of body fluid. Analyte meters may also be configured to determine the concentration of drugs, such as, for example, antibiotics (e.g., gentamicin, vancomycin, and the like), digitoxin, digoxin, drugs of abuse, theophylline, and warfarin, may also be determined and the like, in a sample of body fluid.

Integration with Analyte Meters and/or Analyte Monitoring Systems

In certain embodiments, sensor ports according to the present disclosure are integrated with analyte meters and/or analyte monitoring systems. For example, a sensor port according to the present disclosure may be integrated with a FreeStyle® blood glucose monitoring meter or a Precision® brand blood monitoring meter capable of monitoring glucose and ketones, or other such analytes. In addition, the disclosed sensor ports may find use in meters designed for use in a hospital or similar clinic environment where a single meter may be used for a plurality of patients. Such systems include, but are not limited to, Precision PCx® meters, FreeStyle Connect™ meters and Precision Xceed Pro™ meters manufactured by Abbott Diabetes Care Inc. (Alameda, Calif.).

In certain embodiments, the sensor ports may be integrated with a continuous analyte monitoring system. For example, a continuous glucose monitoring system may include a component that receives analyte data from a transcutaneously positioned or wholly implanted glucose sensor, and which component may be configured to communicate analyte results to the user, e.g., audibly by way of a display, or visually. The continuous monitoring system receiver may include a conventional blood glucose meter and therefore a port for accepting a glucose sensor, e.g., a glucose test strip. The conventional meter and test strip may be used to calibrate the continuous system, e.g., using one point calibration or other calibration protocol. For example, see U.S. Pat. No. 6,175,752, the disclosure of which is incorporated by reference herein.

It should be understood that description of sensor ports in connection with analyte meters includes stand-alone meters, as well those operably connected to, e.g., integrated with, continuous analyte monitoring systems. Exemplary sensors and meters and continuous analyte monitoring systems (sometimes referred to as in vivo systems) that may be utilized in connection with the disclosed sensor ports include sensors and meters such as those described in U.S. Pat. No. 7,041,468; U.S. Pat. No. 5,356,786; U.S. Pat. No. 6,175,752; U.S. Pat. No. 6,560,471; U.S. Pat. No. 5,262,035; U.S. Pat. No. 6,881,551; U.S. Pat. No. 6,121,009; U.S. Pat. No. 7,167,818; U.S. Pat. No. 6,270,455; U.S. Pat. No. 6,161,095; U.S. Pat. No. 5,918,603; U.S. Pat. No. 6,144,837; U.S. Pat. No. 5,601,435; U.S. Pat. No. 5,822,715; U.S. Pat. No. 5,899,855; U.S. Pat. No. 6,071,391; U.S. Pat. No. 6,120,676; U.S. Pat. No. 6,143,164; U.S. Pat. No. 6,299,757; U.S. Pat. No. 6,338,790; U.S. Pat. No. 6,377,894; U.S. Pat. No. 6,600,997; U.S. Pat. No. 6,773,671; U.S. Pat. No. 6,514,460; U.S. Pat. No. 6,592,745; U.S. Pat. No. 5,628,890; U.S. Pat. No. 5,820,551; U.S. Pat. No. 6,736,957; U.S. Pat. No. 4,545,382; U.S. Pat. No. 4,711,245; U.S. Pat. No. 5,509,410; U.S. Pat. No. 6,540,891; U.S. Pat. No. 6,730,200; U.S. Pat. No. 6,764,581; U.S. Pat. No. 6,299,757; U.S. Pat. No. 6,461,496; U.S. Pat. No. 6,503,381; U.S. Pat. No. 6,591,125; U.S. Pat. No. 6,616,819; U.S. Pat. No. 6,618,934; U.S. Pat. No. 6,676,816; U.S. Pat. No. 6,749,740; U.S. Pat. No. 6,893,545; U.S. Pat. No. 6,942,518; U.S. Pat. No. 6,514,718; U.S. Pat. No. 5,264,014; U.S. Pat. No. 5,262,305; U.S. Pat. No. 5,320,715; U.S. Pat. No. 5,593,852; U.S. Pat. No. 6,746,582; U.S. Pat. No. 6,284,478; U.S. Pat. No. 7,299,082; U.S. Patent Application No. 61/149,639, entitled "Compact On-Body Physiological Monitoring Device and Methods Thereof", U.S. patent application Ser. No. 11/461,725, filed Aug. 1, 2006, entitled "Analyte Sensors and Methods"; U.S. patent application Ser. No. 12/495,709, filed Jun. 30, 2009, entitled "Extruded Electrode Structures and Methods of Using Same"; U.S. Patent Application Publication No. US2004/0186365; U.S. Patent Application Publication No. 2007/0095661; U.S. Patent Application Publication No. 2006/0091006; U.S. Patent Application Publication No. 2006/0025662; U.S. Patent Application Publication No. 2008/0267823; U.S. Patent Application Publication No. 2007/0108048; U.S. Patent Application Publication No. 2008/0102441; U.S. Patent Application Publication No. 2008/0066305; U.S. Patent Application Publication No. 2007/0199818; U.S. Patent Application Publication No. 2008/0148873; and U.S. Patent Application Publication No. 2007/0068807; the disclosures of each which are incorporated by reference herein.

Integration with Medication Delivery Devices and/or Systems

In some embodiments, the sensor ports disclosed herein may be included in, e.g., integrated with, a medication delivery system, e.g., an insulin pump module, such as an insulin pump or controller module thereof. Additional information regarding medication delivery devices and/or systems, such as, for example, integrated systems, is provided in U.S. Patent Application Publication No. US2006/0224141, published on Oct. 5, 2006, entitled "Method and System for Providing Integrated Medication Infusion and Analyte Monitoring System", and U.S. Patent Application Publication No. US2004/0254434, published on Dec. 16, 2004, entitled "Glucose Measuring Module and Insulin Pump Combination," the disclosure of each of which is incorporated by reference herein. Medication delivery devices which may be provided with an analyte meter which in turn includes a sensor port as described herein include, e.g., a needle, syringe, pump, catheter, inhaler, transdermal patch, or combination thereof. In some embodiments, the medication delivery device or system may be in the form of a drug delivery injection pen such as a pen-type injection device incorporated within the housing of an analyte meter. Additional information is provided in U.S. Pat. Nos. 5,536,249 and 5,925,021, the disclosure of each of which is incorporated by reference herein.

The medication delivery system may be used for injecting a dose of medication, such as insulin, into a patient based on a prescribed medication dosage, and may be automatically updated with dosage information received from an analyte meter. In another embodiment, the medication dosage of the medication delivery system may include manual entry of dosage changes made through, for example, an optional input unit coupled to the housing of an analyte meter. Medication dosage information associated with the medication delivery system may be displayed on an optional display unit disposed on a housing of an analyte meter.

Integration with Entry Slot Protectors

In some embodiments, the sensor ports described herein can be configured to work with (e.g., engage with or operate in connection with) additional mechanisms and/or devices designed to limit and/or prevent contamination of the internal areas of the sensor ports themselves or the internal areas of the electrical devices into which the sensor ports can be integrated. For example, mechanisms, devices and methods of protecting sensor port openings are described in U.S. Patent Application Publication No. US2008/0234559, and U.S. Patent Application Publication No. US2008/0119709, the disclosure of each of which is incorporated by reference herein. Sensor ports according to the present disclosure can also be configured to be replaceable and/or disposable, and/or configured so as to limit and/or prevent contamination of an electrical device in which the sensor port is integrated. Additional description is provided, for example, in U.S. application Ser. No. 12/495,662, filed Jun. 30, 2009, entitled "Strip Connectors for Measurement Devices;" the disclosure of which is incorporated by reference herein.

Exemplary Sensor Ports

Figure 1A:
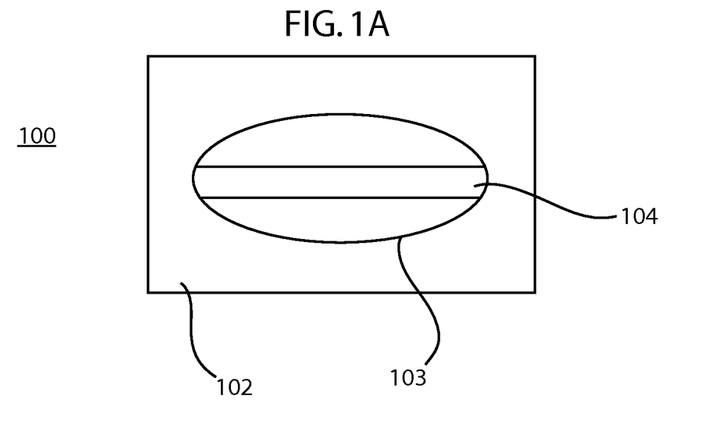
FIGS. 1A, 1B and 1C show a front view, top view and side view respectively of an exemplary embodiment of a sensor port according to the present disclosure.
Figure 1B:
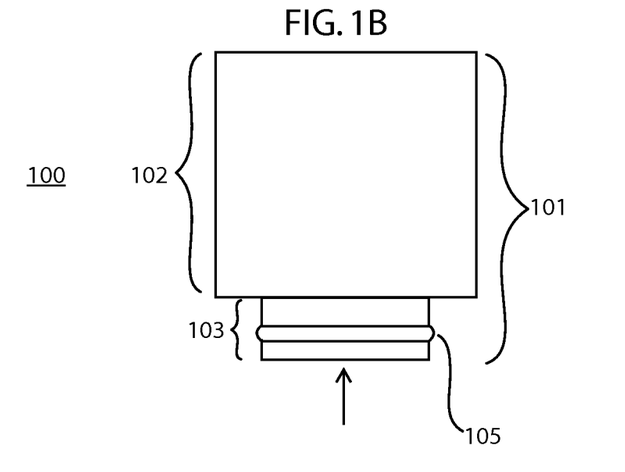
Figure 1C:
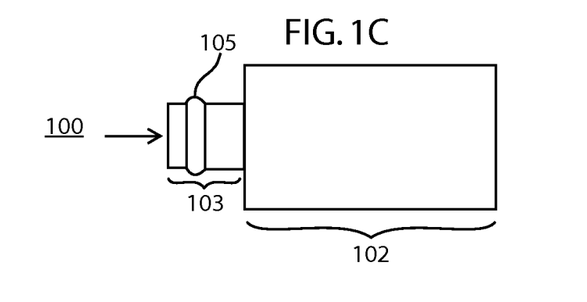

Exemplary sensor ports are now described with reference to the Figures. FIGS. 1A-1C show a sensor port 100, which includes a housing 101, wherein the housing 101 includes a body 102 and a protruding member 103 which protrudes from body 102. Protruding member 103 defines an entry slot 104 which is configured to receive an analyte sensor (shown as an arrow, as depicted in FIGS. 1B and 1C). Protruding member 103 includes a sealing member 105 positioned on protruding member 103 and circumscribing protruding member 103. In other words, sealing member 105 extends around the outside edge of protruding member 103, e.g., as shown in FIGS. 1A-1C. In the embodiments depicted in the Figures, sealing member 105 is illustrated as defining an elliptical shape around the outside edge of protruding member 103. However, a variety of configurations are possible for the protruding member 103 and consequently for the sealing member 105 which circumscribes protruding member 103, e.g., circular, oval, or polygonal configurations.

Figure 8:
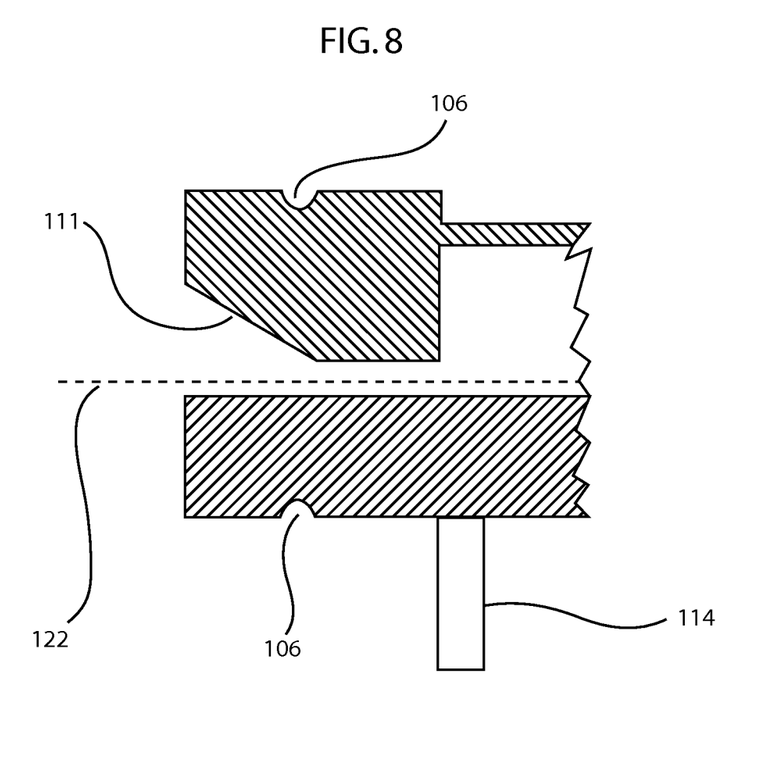
FIG. 8 shows a cross-sectional view of a cut away portion of one embodiment of a sensor port according to the present disclosure, wherein the entry slot includes an internal beveled face.

Entry slot 104 provides access to an internal region of body 102 and is configured to receive an analyte sensor, e.g., an analyte test strip (shown as an arrow, as depicted in FIGS. 1B and 1C). In some embodiments, entry slot 104 includes an internal beveled face 111, e.g., as shown in FIG. 4B and FIG. 8. The angle of the beveled face relative to the plane of insertion 122 can vary. For example, in some embodiments, the angle of the beveled face relative to the plane of insertion 122 is about 25° to about 45°, e.g., about 30° to about 40°. In one specific embodiment, the angle of the beveled face relative to the plane of insertion 122 is about 35°. Inclusion of such a beveled face in entry slot 104 can limit and/or prevent ingress of one or more external contaminants through entry slot 104 and into the internal area of sensor port 100. For example, the presence of internal beveled face 111 may limit and/or prevent splashed fluid material from reaching beyond the beveled portion of beveled face 111, e.g., via deflection of the splashed fluid material away from entry slot 104. It should be noted that entry slot 104 may be any suitable shape. The shape may depend at least in part on the shape of the sensor which the sensor port and/or the electrical device is designed to accept.

Sealing member 105 is configured to form a seal between the sensor port 100 and an electrical device (shown as an arrow, as depicted in FIGS. 1B and 1C) into which the sensor port is integrated or to which the sensor port is attached, e.g., an analyte meter or a medication delivery device. Sealing member 105 may be made of any suitable material. Examples of suitable materials include, but are not limited to, elastomeric materials, e.g., rubber, or other compliant material. In certain embodiments, the material may be a thermoplastic elastomer (TPE), thermoplastic urethane (TPU), polycarbonate (PC), acrylonitrile butadiene-styrene (ABS) or a combination of two or more of these. In some embodiments, sealing member 105 takes the form of a compliant gasket material, e.g., an o-ring made of a suitable material. In some embodiments, sealing member 105 provides a seal between the sensor port 100 and an electrical device into which the sensor port 100 is integrated or to which the sensor port 100 is attached, wherein the seal is a fluid tight seal. For example, the seal may be one which prevents fluid, e.g., water or blood, intrusion between sensor port 100 and an electrical device into which the sensor port 100 is integrated or to which the sensor port 100 is attached. Sealing member 105 may provide a seal between sensor port 100 and an electrical device, wherein the seal is one or more of the following: splash-proof, water-resistant, water repellant and water proof. Thus, in some embodiments, the sealing member 105 resists or does not allow the passage of water, blood, or another liquid between the sensor port 100 and an electrical device. Put another way, sealing member 105 may prevent or at least partially inhibit the ingress of water, blood, or another liquid. In some embodiments, the sealing member 105 reduces by at least about 50%, e.g., at least about 60%, at least about 70%, at least about 80%, at least about 90%, or at least about 99%, the amount of a fluid and/or liquid which would otherwise penetrate, during normal use, between the sensor port 100 and an electrical device into which the sensor port 100 is integrated or to which the sensor port 100 is attached.

The housing 101 can be formed from a variety of suitable materials. For example, a plastic material, e.g., an injection molded plastic material may be utilized. In some embodiments, the material is at least substantially rigid and of a sufficient hardness such that it will not deform under conditions of normal use, e.g., under normal analytical testing conditions. In one specific embodiment, a hot water moldable polyphthalamide (PPA) glass fiber material (available from RTP Company, Winona, Minn.) is utilized as the housing material.

Figure 2:
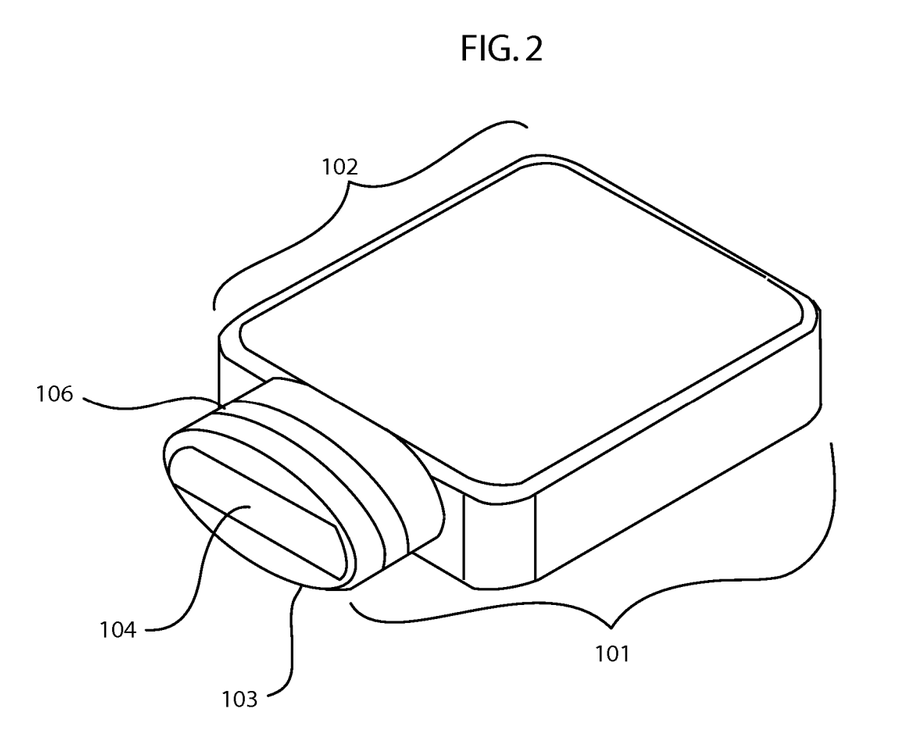
FIG. 2 shows a perspective view of another exemplary embodiment of a sensor port according to the present disclosure.
Figure 3A:
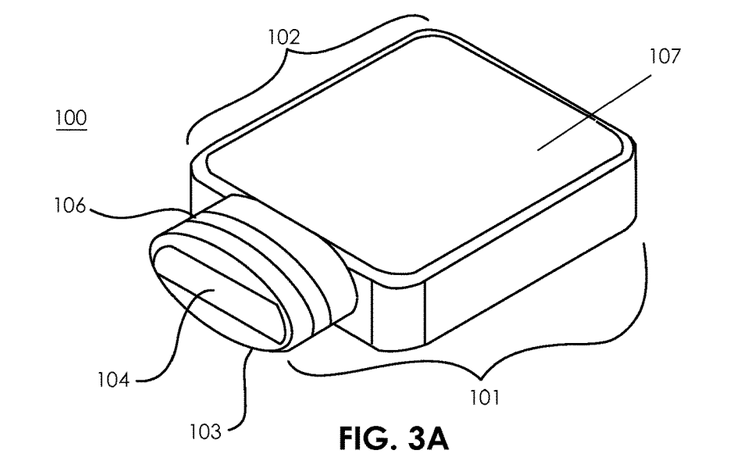
FIGS. 3A, 3B and 3C show a perspective view (3A), a top view (3B), and a bottom view (3C) of an another exemplary embodiment of a sensor port according to the present disclosure.
Figure 3B:
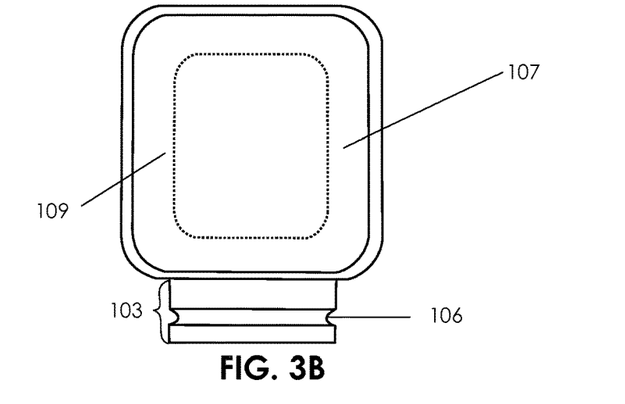
Figure 3C:
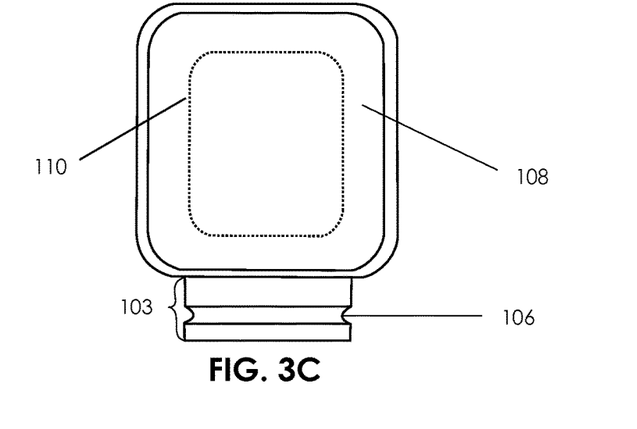

In some embodiments, e.g., as shown in FIGS. 2-5B and 7A-8, protruding member 103 includes a channel 106 which circumscribes the protruding member. In other words, channel 106 extends around the outside edge of protruding member 103, e.g., as shown in FIG. 2. In the embodiment depicted in FIG. 2, channel 106 is illustrated as defining an elliptical shape around the outside edge of protruding member 103. However, a variety of configurations are possible for the protruding member 103, and consequently for the channel 106 which circumscribes protruding member 103, e.g., circular, oval, or polygonal configurations. The channel itself can also take on a variety of configurations, e.g., a half-circle, half-oval or polygonal configuration. The channel 106 provides a location for the deposition and/or positioning of sealing member 105 discussed previously with reference to FIGS. 1A-1C. As such, in some embodiments, the channel 106 is configured based on the shape and size of sealing member 105 or vice versa. Sealing member 105 is configured to form a seal between the sensor port 100 and an electrical device (not shown) into which the sensor port is integrated or to which the sensor port is attached, e.g., an analyte meter or a medication delivery device. As such, it may be desirable for sealing member 105 to fit relatively tightly into channel 106 such that the seal between the sensor port 100 and the electrical device is not compromised.

In some embodiments, e.g., as shown in FIGS. 3A-5B, the body 102 of sensor port 100 defines a first opening 109 and a second opening 110. Openings 109 and 110 can take a variety of shapes depending on the particular application of the sensor port. In some embodiments, openings 109 and 110 provide access to an internal region of the sensor port where one or more internal components may be disposed, e.g., one or more electrical contacts/traces. This access allows for proper placement and/or adjustment of, e.g., the one or more electrical contacts/traces during production of the sensor port 100. The electrical contacts/traces provide a physical and/or electrical interface to an appropriately configured analyte sensor, e.g., an analytical test strip.

In order to limit and/or prevent contamination of the internal region of sensor port 100, e.g., via the ingress of particles and/or fluids through opening 109 and/or 110, in some embodiments, a sealing member 107 is positioned on the body 102 of the housing 101 such that a seal is formed over the first opening 109. Another sealing member 108 is positioned on the body 102 of the housing 101 such that a seal is formed over the second opening 110. See, e.g., FIGS. 3A-3C and 6A-7B. In operation, sealing members 107 and 108 can limit and/or prevent ingress of one or more fluids, particles, or other contaminants through openings 109 and 110. Sealing members 107 and 108 may provide a seal, wherein the seal is one or more of the following: splash-proof, water-resistant, water-repellant and water-proof. Thus, in some embodiments, sealing members 107 and 108 resist or do not allow the passage of water, blood, or another liquid through openings 109 and 110 respectively. Put another way, sealing members 107 and 108 may prevent or at least partially inhibit the ingress of water, blood, or another liquid through openings 109 and 110 respectively. In some embodiments, the sealing members 107 and 108 reduce by at least about 50%, e.g., at least about 60%, at least about 70%, at least about 80%, at least about 90%, or at least about 99%, the amount of a fluid and/or liquid which would otherwise penetrate, during normal use, through openings 109 and 110 respectively. In other embodiments, e.g., as shown in FIGS. 1A-1C and FIG. 2, body 102 lacks any openings to the environment external to body 102 other than that provided by entry slot 104 and is thus sealed without the use of additional sealing members on body 102.

A variety of suitable materials may be used for sealing members 107 and 108, provided they are capable of limiting and/or preventing ingress of one or more fluids, particles, or other contaminants through openings 109 and 110. For example, suitable materials include, but are not limited to, one or more natural or synthetic polymers. In some embodiments, it may be desirable to use a material which includes a pre-applied adhesive, e.g., a silicone adhesive, in order to facilitate attachment of the sealing member to the body 102 of sensor port 100. Alternatively, a suitable adhesive can be applied separately. In one embodiment, a suitable material for use as sealing member 107 and/or 108 is polyimide film tape, such as that available from 3M Corporation (St. Paul, Minn.).

In some embodiments, as shown, for example, in FIGS. 4A-5B, a housing 101 of a sensor port 100 includes a top portion 112 and a bottom portion 113 which are joined to form sensor port 100. Top portion 112 and bottom portion 113 can be joined, for example, by inserting optional connection stilts 114 on top portion 112 through optional connection stilt insertion holes 115 on bottom portion 113.

As illustrated in FIGS. 4A, 4B, 5A, 5B, 7A and 7B, an exemplary embodiment of a sensor port 100 according to the present disclosure is described with respect to a specific electrical contact/lead configuration. It should be noted, however, that a variety of such configurations are known in the art, as evidenced by the patents, patent applications, and patent application publications incorporated by reference herein. The sensor ports according to the present disclosure may be readily configured to accommodate a variety of such configurations. For example, in one embodiment, a sensor port according to the present disclosure can be configured as a "Smart Sensor Port" as described in U.S. patent application Ser. No. 12/431,672, filed Apr. 28, 2009, and entitled "Smart Sensor Ports and Methods of Using Same," the disclosure of which is incorporated by reference herein.

Figure 4A:
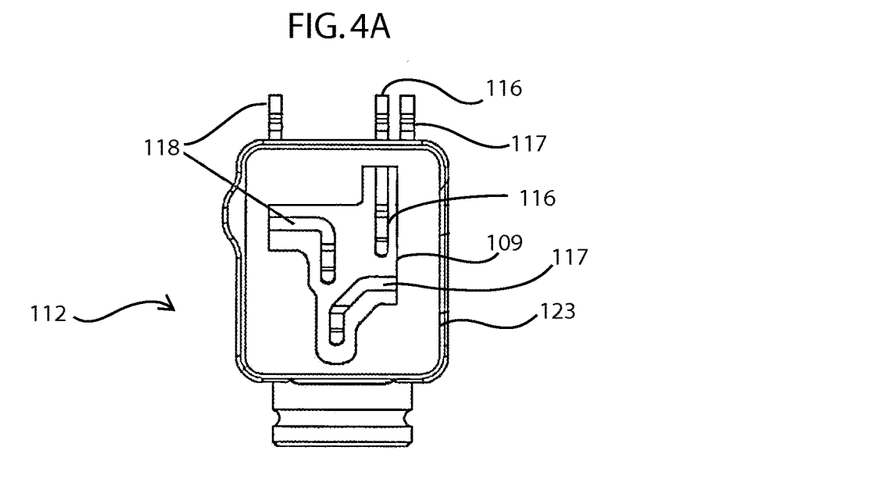
FIGS. 4A and 4B depict a top portion of the housing for another exemplary embodiment of a sensor port according to the present disclosure, wherein the top portion of the housing is shown top side up (4A) and bottom side up (4B)
Figure 4B:
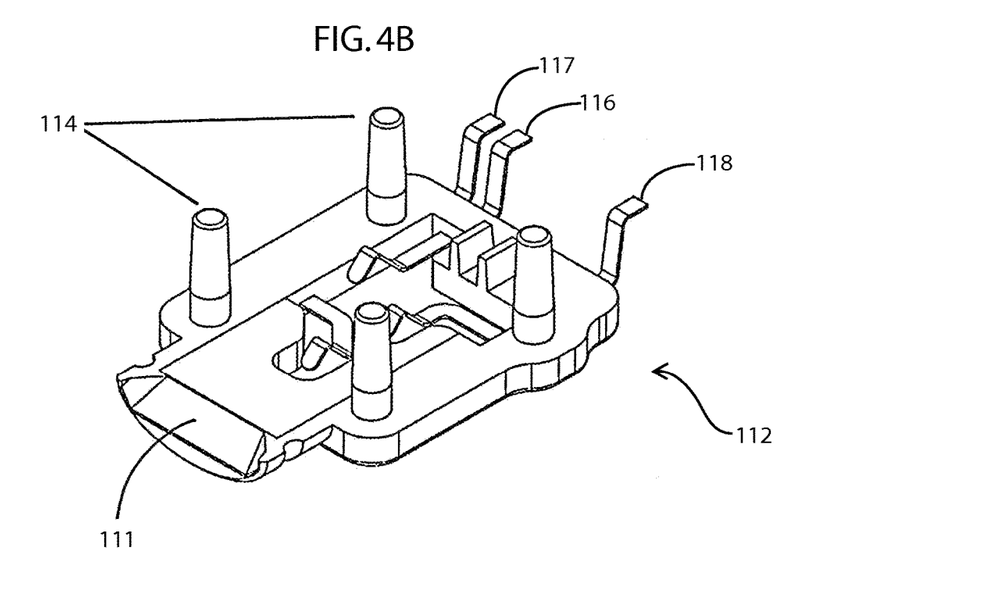

FIGS. 4A and 4B show three electrical contacts/leads (116, 117 and 118) incorporated into top portion 112 of housing 101. In one embodiment, electrical contact 116 is configured to contact a working electrode lead of an analyte sensor (not shown) when the analyte sensor is inserted into entry slot 104 of an assembled sensor port 100.

Electrical contacts/leads 117 and 118 are optional electrical contacts/leads which can be configured such that upon insertion of an analyte sensor (not shown) optional electrical contacts/leads 117 and 118 contact an optional insertion monitor (not shown) positioned on the analyte sensor as described, for example, in U.S. Pat. No. 6,616,819, the disclosure of which is incorporated by reference herein; and/or a turn-on/selection monitor as described, for example, in U.S. application Ser. No. 12/431,672, filed Apr. 28, 2009, and entitled "Smart Sensor Ports and Methods of Using Same," the disclosure of which is incorporated by reference herein. Additional description of insertion monitors and configurations suitable for use as turn-on/selection monitors is provided, for example, in U.S. Patent Application Publication No. US2006/0091006; U.S. Patent Application Publication No. US2008/0267823; U.S. Patent Application Publication No. US2009/0011449; U.S. Patent Application Publication No. US2008/0066305; U.S. Patent Application Publication No. US2008/0060196; U.S. Pat. No. 6,592,745; U.S. Pat. No. 6,143,164; U.S. Pat. No. 6,071,391; U.S. Pat. No. 6,503,381; and U.S. Pat. No. 6,893,545; the disclosures of each of which are incorporated by reference herein.

Figure 5A:
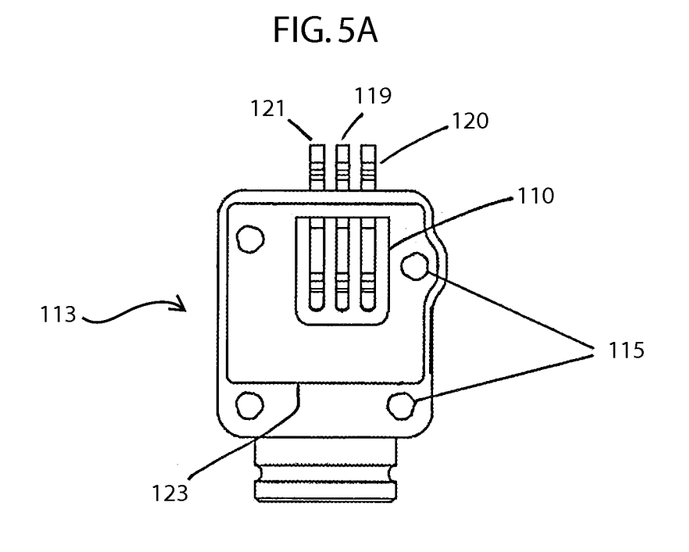
FIGS. 5A and 5B depict a bottom portion of the housing for the sensor port embodiment referenced for FIGS. 4A and 4B, wherein the bottom portion of the housing is shown bottom side up (5A) and top side up (5B)
Figure 5B:
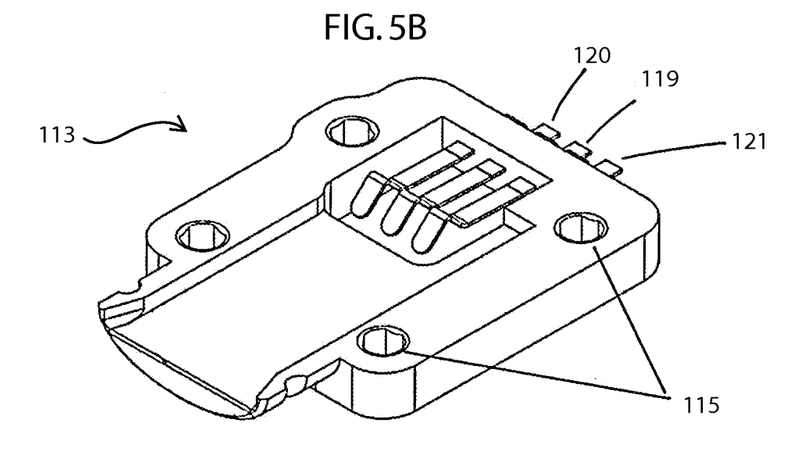
Figure 6A:
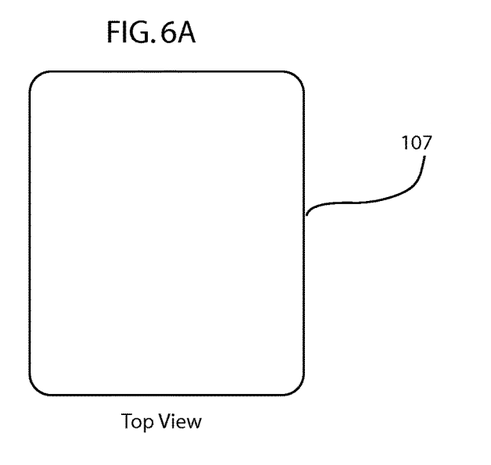
FIGS. 6A, 6B, 6C and 6D show a first sealing member top view (6A), a first sealing member side view (6B), a second sealing member top view (6C) and a second sealing member side view (6D) of the sensor port embodiment referenced in FIGS. 4A, 4B, 5A and 5B.
Figure 6B:
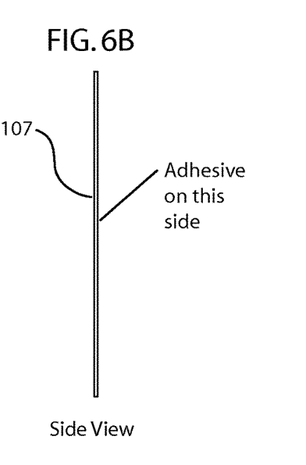
Figure 6C:
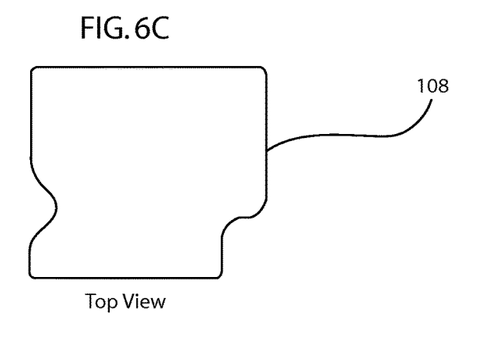
Figure 6D:
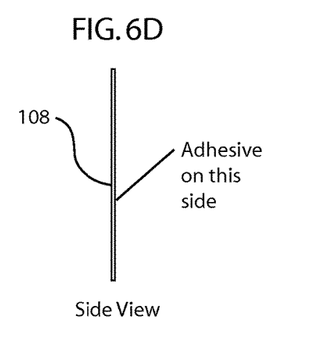

FIGS. 5A and 5B show three electrical contacts/leads (119, 120, and 121) incorporated into bottom portion 113 of housing 101. In one embodiment, electrical contact 119 is configured to contact a reference/counter electrode lead of an analyte sensor (not shown) when the analyte sensor is inserted into entry slot 104 of an assembled sensor port 100. As used herein, the term "reference/counter electrode" refers to an electrode that functions as a reference electrode, a counter electrode, or both a reference and a counter electrode.

Electrode contacts/leads 120 and 121 are optional electrical contacts/leads which can be configured such that upon insertion of an analyte sensor (not shown) optional electrical contacts/leads 120 and 121 contact optional fill indicator electrode leads (not shown) of an analyte sensor (not shown), e.g., as described in U.S. Pat. No. 6,616,819, the disclosure of which is incorporated by reference herein.

Figure 7A:
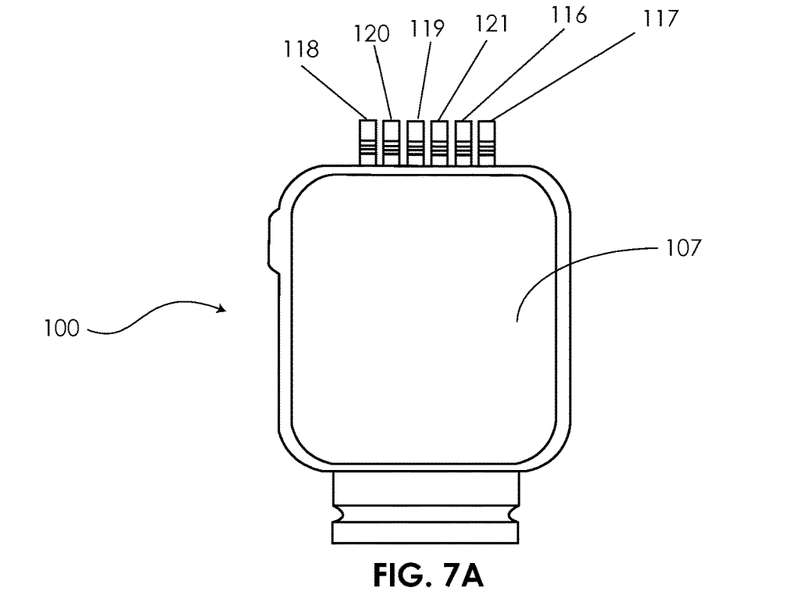
FIGS. 7A and 7B show a top view (7A) and a bottom view (7B) of the sensor port embodiment referenced in FIGS. 4A, 4B, 5A, 5B, 6A and 6B, wherein first and second sealing members are depicted positioned on the top and bottom portions of the sensor port housing respectively.
Figure 7B:
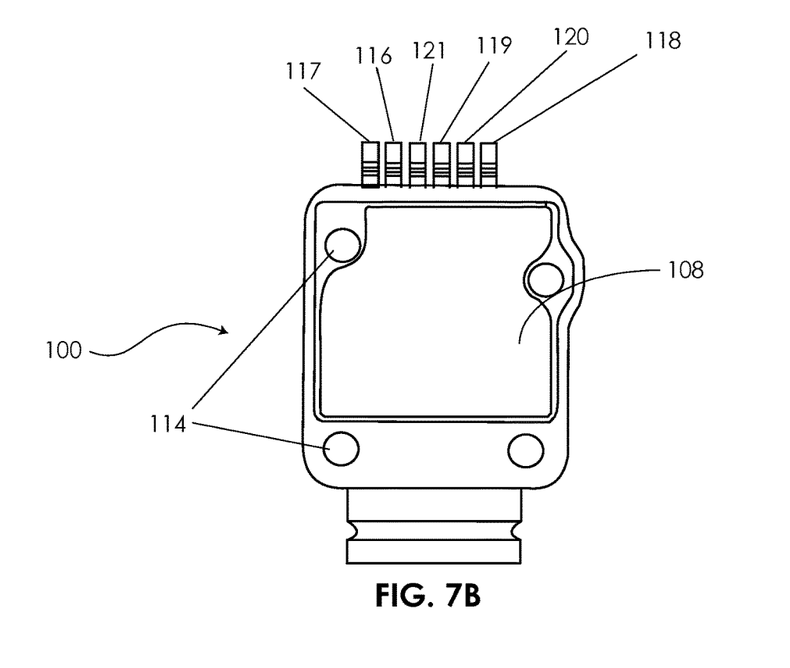

FIGS. 6A, 6B, 7A and 7B show exemplary embodiments of sealing member 107 and sealing member 108. In the depicted embodiments, first and second sealing members 107 and 108 are shaped and sized such that they completely cover and seal first opening 109 and second opening 110 respectively. Although particular configurations are shown in the Figures, it should be noted that sealing members 107 and 108 can have a variety of suitable configurations and/or shapes depending on the particular configuration of one or more of housing 101, body 102 and openings 109 and 110. For example, as shown in FIG. 7B, in one embodiment, sealing member 108 has an irregular shape which allows it to completely cover and seal second opening 110 while simultaneously leaving uncovered the area of body 102 where the connection stilts 114 and the connection stilt insertion holes 115 are positioned. In some embodiments, body 102 of housing 101 is configured to include depressed regions which facilitate proper positioning of sealing members 107 and 108 over openings 109 and 110. Exemplary depressed regions are shown in FIGS. 4A and 5A where they are indicated as bounded by edge 123.

The preceding merely illustrates the principles of the invention. It will be appreciated that those skilled in the art will be able to devise various arrangements which, although not explicitly described or shown herein, embody the principles of the invention and are included within its spirit and scope. Furthermore, all examples and conditional language recited herein are principally intended to aid the reader in understanding the principles of the invention and the concepts contributed by the inventors to furthering the art, and are to be construed as being without limitation to such specifically recited examples and conditions. Moreover, all statements herein reciting principles, aspects, and embodiments of the invention as well as specific examples thereof, are intended to encompass both structural and functional equivalents thereof. Additionally, it is intended that such equivalents include both currently known equivalents and equivalents developed in the future, i.e., any elements developed that perform the same function, regardless of structure. The scope of the present invention, therefore, is not intended to be limited to the exemplary embodiments shown and described herein. Rather, the scope and spirit of present invention is embodied by the appended claims.

That which is claimed is:

1. An analyte meter and sensor port, comprising:
   the sensor port integratable and connectable to the analyte meter and including a housing, the housing comprising:
   a body; and
   a protruding member, the protruding member extending from the body and having a distal end,
   wherein the distal end comprises an entry slot to receive an analyte sensor; and
   a first sealing member circumscribing the protruding member and positioned wholly between the entry slot and the body,
   wherein the first sealing member forms a seal between the sensor port and the analyte meter.

2. The analyte meter and sensor port of claim 1, wherein the body defines a first opening and a second opening, and the sensor port further comprises:
   a second sealing member positioned on the body such that a seal is formed over the first opening; and
   a third sealing member positioned on the body such that a seal is formed over the second opening.

3. The analyte meter and sensor port of claim 2, wherein the second and third sealing members each comprise an adhesive backing which provides for attachment to the body of the housing.

4. The analyte meter and sensor port of claim 3, wherein the second and third sealing members each comprise polyimide film tape.

5. The analyte meter and sensor port of claim 1, wherein a channel which circumscribes the protruding member between the entry slot and the body, and wherein the first sealing member is positioned in the channel.

6. The analyte meter and sensor port of claim 5, wherein the channel defines an oval.

7. The analyte meter and sensor port of claim 6, wherein the distal end comprising the entry slot is a flush surface and defines an oval.

8. The analyte meter and sensor port of claim 1, wherein the analyte meter is a glucose meter.

9. The analyte meter and sensor port of claim 1, wherein the first sealing member is a compliant gasket material.

10. The analyte meter and sensor port of claim 9, wherein the compliant gasket material comprises an elastomeric material.

11. The analyte meter and sensor port of claim 9, wherein the compliant gasket material is an o-ring.

12. The analyte meter and sensor port of claim 1, wherein a first edge of the entry slot comprises an internal beveled face.

13. The analyte meter and sensor port of claim 12, wherein a second edge of the entry slot is curved and a third edge of the entry slot is curved and opposite the second edge.

14. The analyte meter and sensor port of claim 12, wherein a second edge of the entry slot does not comprise an internal beveled face.

15. The analyte meter and sensor port of claim 12, wherein a second and third edge of the entry slot each comprise an internal beveled face.

16. The analyte meter and sensor port of claim 1, wherein the distal end comprising the entry slot is a flush surface and has the same shape as the first sealing member.

17. The analyte meter and sensor port of claim 1, wherein the housing comprises a top portion and a bottom portion which are joined to form the sensor port.

18. The analyte meter and sensor port of claim 1, wherein the sensor port is integrated in and operably connected to the analyte meter.

19. The analyte meter and sensor port of claim 1, wherein the first sealing member provides a substantially fluid-tight seal between the sensor port and the analyte meter.

* * * * *